United States Patent [19]

Detoro

[11] Patent Number: 5,088,479
[45] Date of Patent: Feb. 18, 1992

[54] ANKLE AND FOOT ORTHOSIS

[76] Inventor: William W. Detoro, 930 Trailwood Dr., Boardman, Ohio 44512

[21] Appl. No.: 514,738

[22] Filed: Apr. 26, 1990

[51] Int. Cl.$^5$ .............................................. A61F 5/00
[52] U.S. Cl. ...................................................... 602/27
[58] Field of Search ............... 128/68, 75, 80 E, 80 R, 128/80 H, 83, 83.5, 84 R, 85, 87 R, 89 R, 90, 165, 166

[56] References Cited

U.S. PATENT DOCUMENTS

| | | | |
|---|---|---|---|
| 2,847,991 | 8/1958 | Andrews. | |
| 3,606,884 | 9/1971 | Peter. | |
| 3,618,946 | 11/1971 | Lee et al. | |
| 3,680,552 | 8/1972 | Bell et al. | 128/75 X |
| 3,976,059 | 8/1976 | Lonardo. | |
| 4,178,925 | 12/1979 | Hirt | 128/83.5 |
| 4,366,812 | 1/1983 | Nuzzo | 128/77 |
| 4,476,858 | 10/1984 | Curtis | 128/165 X |
| 4,771,768 | 9/1988 | Crispin | 128/80 H |
| 4,886,258 | 12/1989 | Scott | 128/87 R X |
| 4,938,777 | 7/1990 | Mason et al. | 128/80 H X |

FOREIGN PATENT DOCUMENTS 1454461  1/1989  U.S.S.R. ................ 128/80 H

*Primary Examiner*—Richard J. Apley
*Assistant Examiner*—Linda C. M. Dvorak
*Attorney, Agent, or Firm*—Harpman & Harpman

[57] ABSTRACT

An ankle and foot orthosis device for use in support, protection and partial immobilization of the ankle/foot complex comprising a multiple part L-shaped construction having a contoured lower leg engagement portion and a two-part foot engagement portion interconnected by an adjustable resilient heel enclosing member. This device has a releaseable foot enclosure that secures the device to the foot.

5 Claims, 2 Drawing Sheets

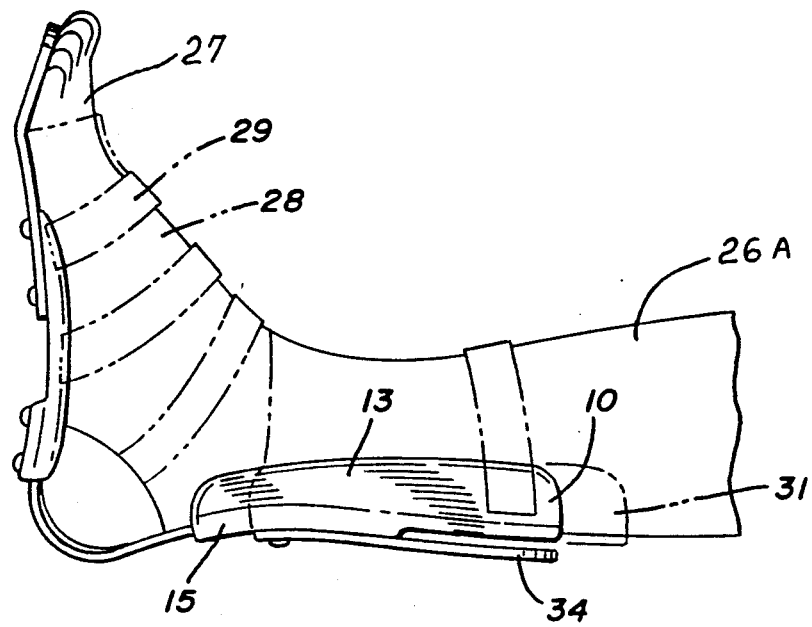
FIG. 1
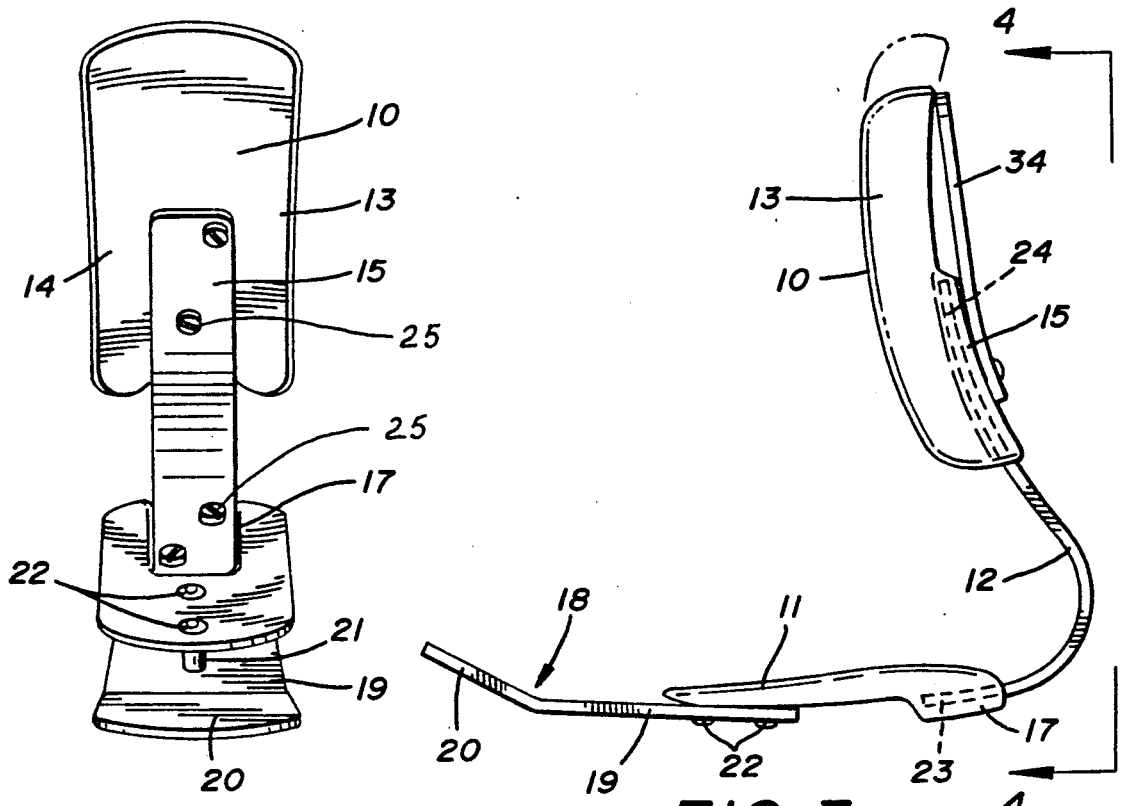
FIG. 2
FIG. 3

ANKLE AND FOOT ORTHOSIS

BACKGROUND OF THE INVENTION

1. Technical Field

This device relates to therapeutic leg and foot braces and supports that are used to place precise and consistent pressure on the sole and calf for therapeutic purposes and to partially immobilize the ankle/foot complex in a predetermined and advantageous position.

2. Description of Prior Art

Prior Art devices of this type have relied on a variety of construction configurations that support and hold and immobilize the foot and lower leg portion of the patient. See for example U.S. Pat. Nos. 3,976,059, 3,618,946, 3,606,884 and 2,847,991.

In U.S. Pat. No. 3,976,059 a leg and foot device can be seen having a contoured one-piece L-shaped member engageable on the lower leg and the bottom of the foot. The upper portion is contoured to fit the leg and the heel portion of the foot. A releaseable attachment means secures the foot and leg in fixed position relative to each other on the device.

In U.S. Pat. No. 3,618,946 an insert for a football kicking shoe can be seen having a one-piece contoured leg and foot engagement portion to be placed inside the shoe for additional support during sporting activities.

U.S. Pat. No. 3,606,884 discloses a foot boot apparatus having a pair of spaced interconnected L-shaped brackets for receiving and supporting a patient's foot within a soft boot configuration secured by velcro bands and fastener strips.

In U.S. Pat. No. 2,847,991 a drop foot brace can be seen having a contoured foot portion and a leg spring strip extending at angles therefrom. An elongated strap is extended around the foot and leg spring holding a patient's foot in place on the device.

SUMMARY OF THE INVENTION

A multi-part therapeutic device that is adjustably secured to the foot and leg of a patient that allows for a variable incremental resilient adjustment between the leg and foot portion by interchangeable stiffening bars interconnecting therebetween is disclosed. Length and height adjustment for the leg and foot portion respectively can be made independent of the required resiliency by multi-part extension on the foot portion. The leg portion can be extended from the point of interconnection between the stiffening bar and same.

DESCRIPTION OF THE DRAWINGS

FIG. 1 is a side elevational view of the device engaged on a patient;

FIG. 2 is a top perspective view of the device independent of the patient;

FIG. 3 is a side plan view of the device shown in FIG. 2;

DESCRIPTION OF THE PREFERRED EMBODIMENT

Figure 4:
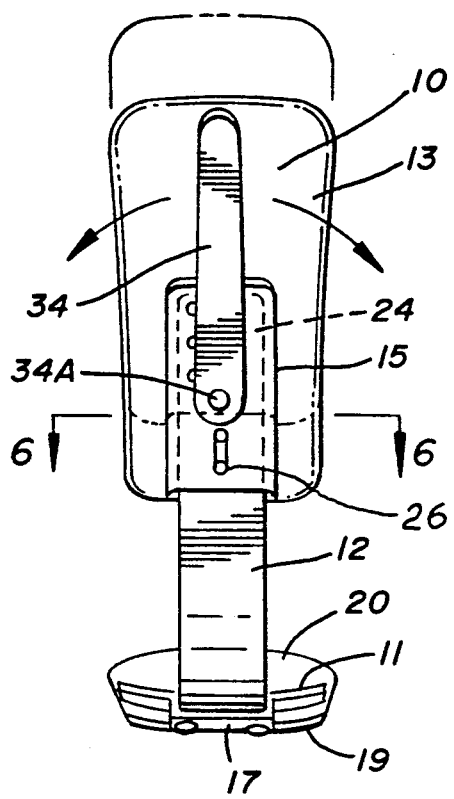
FIG. 4 is a plan view on lines 4—4 of FIG. 3.

Referring to FIGS. 1-4 of the drawings the orthotics device can be seen comprising a multiple part construction having a leg portion 10, a foot portion 11 and an innterconnecting member 12 therebetween. The leg portion 10 has a proximal and distal end with contoured oppositely disposed elongated side areas 13 and 14. An elongated recessed channel 15 is formed within the leg portion 10 extending inwardly from its distal end to a distance equal to approximately one-half its overall length. The foot portion 11 has a generally rectangular configuration with contoured sides 16 with a recessed pocket 17 in one end thereof.

An extension member 18 is adjustably secured to the foot portion 11 opposite said pocket 17. The extension member 18 has a flat base area 19 with an upturned end portion 20 with a mounting slot at 21 aligned for registration with adjustable fittings 22 extending from said foot portion 11 as best seen in FIGS. 2-4 of the drawings.

It will be evident from the above description that the extension member 18 can be extended to effectively lengthen said foot portion 11 as indicated in FIG. 3 of the drawings.

The interconnecting member 12 is comprised of a resilient metal alloy or alternately a carbon fiber laminate formed in a compound curved generally L-shaped configuration having free ends 23 and 24. The respective free ends 23 and 24 of said interconnecting member 12 are engaged respectively in said recessed pocket 17 and said recessed channel 15. Pairs of removable fasteners 25 extend from the respective ends 23 and 24 and register with fixed apertures in said pocket 17 and adjustably in elongated slots 26 in said channel 15 so as to provide for lateral extension of leg portion 10 as depicted in broken lines in FIGS. 2 and 3 of the drawings.

Since the interconnection member 12 can readily removed, a variety of substitute interconnecting members 12 can be used each of which has different degrees of rigidity defining the overall resiliency between said leg and foot portions as hereinbefore described.

Figure 5:
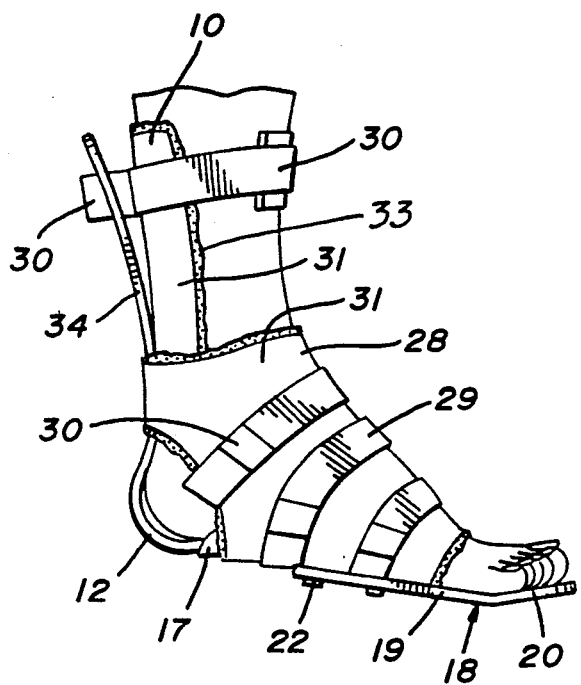
FIG. 5 is a perspective view of the device on a patient in an upright position.
Figure 6:
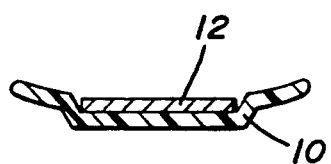
FIG. 6 is a partial cross-sectional view on lines 6—6 of FIG. 4.

The leg and foot portions are made of a plastic resin material so as to be molded or preformed into a desired contoured configuration required for engagement with the patient's leg 26A and foot 27 as seen in FIGS. 1 and 5 of the drawings.

A fabric sleeve 28 is slit along its length and has associated spaced fixation straps 29 thereon which are used to secure the sleeve to the invention and the patient's leg and foot 26A and 27 respectively. The patient's foot 27 has a heel portion 27A.

The fixation straps 29 have respective velcro band end fasteners at 30 which will be well understood by those skilled in the art.

The fabric sleeve 28 includes a fabric leg engagement portion 31 that is positioned inside the plastic leg portion 10. It should be noted that the fabric sleeve 28 extends over and encompasses a section of the plastic leg portion 10 and the foot portion 11. The foot extension 18 is positioned over the fabric sleeve 28 so as to be free for lateral adjustment as noted above. The fabric sleeve 28 is lined with a soft synthetic fur-like material 33 for comfort and configuration to the relatively unyielding plastic resin leg and foot portions 10 and 11.

In order to restrict or reduce rotation of the patient's foot, if required, a stabilization arm 34 is pivotally attached to and extends longitudinally from the plastic leg portion 10. The stabilization arm 34 can be rotated about a pivot point 34A in an arcuate path indicated by the arrows in FIG. 4 of the drawings. Since the interconnecting member 12 can be removably replaced with substitute members having varied resilient qualities as noted above the relative flex between the leg and foot portions can be varied as required under different physical support requirements greatly enhancing the usefulness and effectiveness of the orthotics device.

Thus, it will be seen that a new and useful device has been illustrated and described to provide a therapeutic leg and foot device of basic construction that can be adjusted to fit the patient and provide a secure, safe, useful and comfortable support.

It will be apparent to those skilled in the art that various changes and modifications may be made therein without departing from the spirit of the invention, therefore I claim:

1. A therapeutic leg and foot device comprising a leg portion and a foot portion interconnected by a resilient member at right angles to one another, said resilient member comprises a flat metallic bar configuration having a compound L-shaped curved configuration adjacent one end thereof, said leg portion is of a generally contoured elongated channel shape of thermoplastic material with an elongated pocket formed in one end thereof for removable registration with said resilient member, a foot extension longitudinally advanced from one end of said foot portion, said foot extension having a generally flat base portion and an upturned and portion, said foot portion comprising a generally rectangular configuration having contoured sides, and a recessed pocket in the free end thereof for fixed registration with said resilient member, in spaced relation to said compound L-shaped curved configuration, means for adjustably securing said interconnecting resilient member to said leg portion and said foot extension to said foot portion, means for releaseably securing the device to the leg and foot of a patient.

2. The therapeutic leg and foot device of claim 1 wherein said leg portion is provided with a stabilization arm pivotally secured thereto and extending therefrom.

3. The therapeutic leg and foot device of claim 1 wherein said means for adjustably securing said interconnecting resilient member to said leg portion comprises adjustable fasteners.

4. The therapeutic leg and foot device of claim 1 wherein said means for releaseably securing said device to said leg and foot of said patient comprises a fabric sleeve having plurality of adjustable fixation straps engaged on said device and said foot and leg portion.

5. The therapeutic leg and foot device of claim 1 wherein said resilient member is interchangeable and wherein said compound L-shaped curved configuration is adjacent a patient's heel portion.

* * * * *